United States Patent [19]

Hauck et al.

[11] 3,953,434

[45] Apr. 27, 1976

[54] DIENES USEFUL IN THE PREPARATION OF 1,2,3,4,4A,5,6,7-OCTAHYDRO-7-ARYL-ISOQUINOLINES

[75] Inventors: Frederick Peter Hauck, Somerville, N.J.; Joseph E. Sundeen, Yardley, Pa.

[73] Assignee: E. R. Squibb & Sons, Inc., Princeton, N.J.

[22] Filed: Apr. 11, 1975

[21] Appl. No.: 567,347

Related U.S. Application Data

[62] Division of Ser. No. 295,385, Oct. 5, 1972, Pat. No. 3,901,897.

[52] U.S. Cl................. 260/240 D; 260/283 S; 260/283 CN; 260/283 SY; 260/287 R; 260/289 R; 260/290 R; 260/290 H; 260/294.8 B; 260/294.8 D; 260/288 R; 260/295 R; 424/258
[51] Int. Cl.².................................. C07D 211/70
[58] Field of Search............................ 260/240 D

[56] References Cited
UNITED STATES PATENTS 2,558,777  7/1951  Papa et al.................. 260/240 D
3,179,559  4/1965  Wood et al.................. 260/240 D

FOREIGN PATENTS OR APPLICATIONS 2,101,998  8/1972  Germany

OTHER PUBLICATIONS

Schmidle et al., J. Am. Chem. Soc., 78 (1956) pp. 425–428.

Primary Examiner—Arthur P. Demers
Attorney, Agent, or Firm—Lawrence S. Levinson; Merle J. Smith; Stephen B. Davis

[57] ABSTRACT

Dienes of the formula

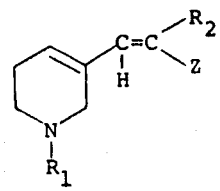

wherein $R_1$ and $R_2$ are hydrogen, lower alkyl, lower alkenyl, aryl-lower alkyl, aryl-lower alkenyl, or heterocycle and Z is phenyl, substituted phenyl, naphthalene or heterocycle are disclosed. These compounds are useful as intermediates in the preparation of various pharmaceutically active 1,2,3,4,-4a,5,6,7-octahydro-7-aryl-isoquinolines.

9 Claims, No Drawings

DIENES USEFUL IN THE PREPARATION OF 1,2,3,4,4A,5,6,7-OCTAHYDRO-7-ARYL-ISOQUINOLINES

This application is a division of Ser. No. 295,385 filed on Oct. 5, 1972, now U.S. Pat. No. 3,901,897.

There is a continuing search for new chemotherapeutic agents.

This invention relates to blood pressure lowering reagents, anti-inflammatory reagents, antianginal and antiarrhythmic agents of the following general formula:

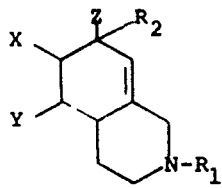

IV wherein Z is phenyl, substituted phenyl, (wherein said substituent is lower alkyl, lower alkoxy, nitro, halogen, trifluoromethyl, cyano, carbo-lower alkoxy, carboxy, etc.), naphthalene, aromatic type heterocycle such as pyridine, pyrrole, furan, thiophene, imidazole, thiadiazole, etc., $R_1$ and $R_2$ are hydrogen, lower alkyl, lower alkenyl, aryl-lower alkyl, aryl-lower alkenyl and heterocyclyl; X and Y are hydrogen, carboxyl, carboxamido, carbo-lower alkoxy, carbonyl, nitro, hydroxy, cyano, amino, mono- and di-lower alkyl amino, hydroxy methyl, lower acyloxymethyl, lower alkoxymethyl, aminomethyl, arylsulfonoxymethyl or halomethyl; X may be joined to Y to give rise to ring systems wherein X–Y is:

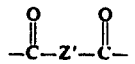

wherein Z' is NH,NR, oxygen, sulfur, —CH=CH—, —CH$_2$—, or —CH$_2$—CH$_2$, or —CH$_2$—Z$^2$—CH$_2$— wherein Z$^2$ is oxygen, sulfur, —CH=CH—, —CH$_2$—, —CH$_2$—CH$_2$—, —NH— or —NR— wherein R is lower alkyl, aryl or aryl-loweralkyl and pharmaceutically acceptable salts thereof (hydrochloride, sulfate, phosphate, acetate, citrate, tartrate, etc.).

In addition, this invention encompasses methods for preparing said compounds, the compositions containing said compounds and methods for using said compositions.

Lastly, this invention relates to the novel dienes used to prepare the useful compounds of this invention.

The term loweralkyl is intended to mean a straight or branched chain alkyl group of from one to eight carbon atoms.

The term lower alkoxy is intended to mean a straight or branched chain alkyl group of from one to eight carbon atoms linked directly to an oxygen atom.

The term aryl is intended to mean phenyl, naphthyl and substituted phenyl or naphthyl.

The term substituted when applied to aryl or phenyl is intended to encompass one or two substituents which may be alike or different and are selected from the following group, lower alkyl, lower alkoxy, nitro, halogen, trifluoromethyl, cyano, carbo-lower alkoxy and carboxy.

The compounds of the present invention may exist in a number of isomeric forms such as stereoisomeric forms, endo and exo forms, etc. In addition position isomers of these compounds are disclosed in copending application Ser. No. 295,386 filed Oct. 5, 1972, now abandoned.

The preferred compounds of this invention are those wherein the functional groups are $R_1 = CH_3$; $R_2 = H$; X and Y are carboxyl, hydroxylmethyl and taken together to form

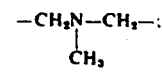

Z is phenyl and methoxyphenyl.

The compounds of this invention may be prepared by the following reaction sequence:

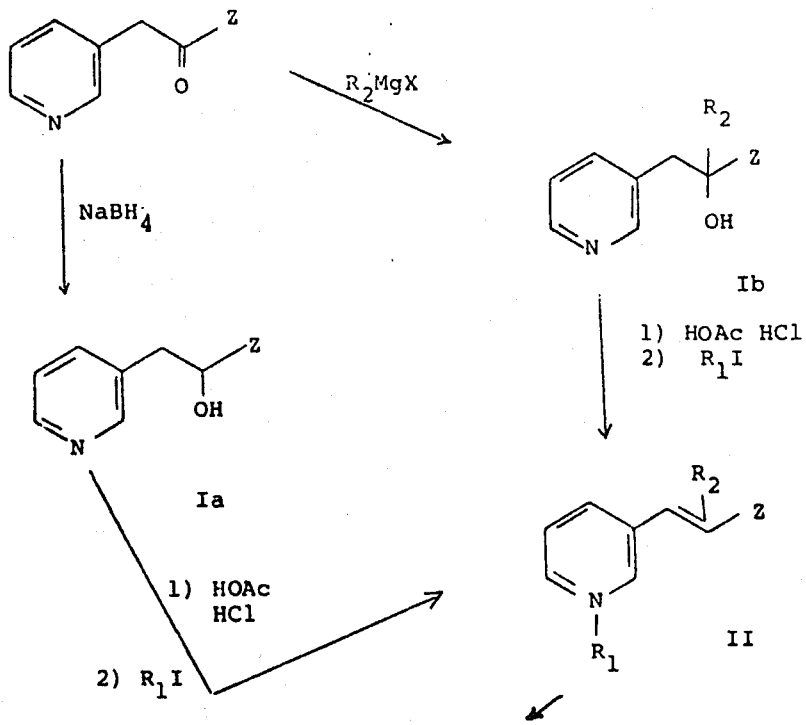

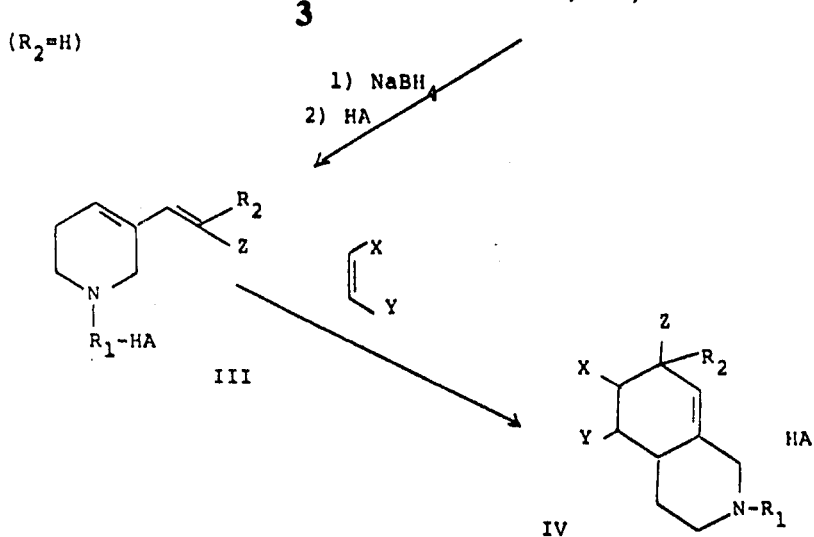

The initial starting materials are prepared according to the procedures shown in The Journal of the American Chemical Society 78, 674 (1956) and 82, 472 (1960). These compounds may be converted to the secondary alcohols Ia by a sodium borohydride reduction in an aqueous alcohol or tertiary alcohols Ib by a standard Grignard Reaction. The alcohols are dehydrated utilizing a refluxing hydrochloric acid-acetic acid mixture followed by quaternization with an alkyl iodide using a nitrile as the solvent. The compounds of the type II which are obtained are again reduced with sodium borohydride in an aqueous alcohol to give compounds of the type III.

This invention teaches the procedures for reacting compounds of the type III with most dienophiles and obtain the desired Diels-Alder Adduct of the type IV, wherein Z, $R_1$, $R_2$, X and Y are as previously described and HA is a strong acid, such as hydrochloric acid, sulfuric acid, phosphoric acid, p-toluenesulfonic acid, etc.

The reactions are generally carried out in a lower-alkanoic acid-lower alkanoic acid anhydride mixture, such as acetic acid-acetic anhydride, butyric acid - butyric anhydride, acetic acid - propionic anhydride, etc. at a temperature range of from about 75° to about 175°C, preferably 120° to 140°C. Reaction rates vary considerably; however, the reactions can be followed by way of thin film chromatography and are continued until completion which is usually within a 24 hour period.

Typical dienophiles which may be employed in the process of this invention are given in Organic Reactions, Vol. IV, p.2-3, more specifically maleic anhydride, maleic acid, furmaric acid, diethyl maleate, diethyl fumerate, maleimide, N-substituted maleimides, acrylonitrile, ethyl acrylate, acrylic acid, etc.

The dienes are used in the form of a salt of a strong acid and the amino group is trisubstituted. Some typical examples of dienes which may be employed in the process of this invention are 1-methyl-5-styryl-1,2,3,6-tetrahydropyridine, 1-benzyl-5-p-methoxystyryl-1,2,3,6-tetrahydropyridine, and 1-allyl-5-p-nitrostyryl-1,2,3,6-tetrahydropyridine.

In addition, the processes for converting the Diels-Alder Adducts into other useful compounds is taught. Thus the product (IVa) formed by the reaction betweeen maleic anhydride and a compound of the type III may be converted into numerous other useful products (V – X) according to the following reaction sequence:

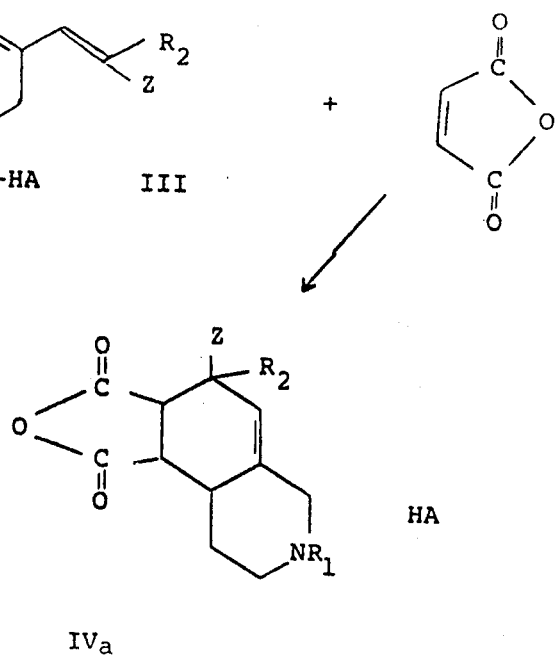

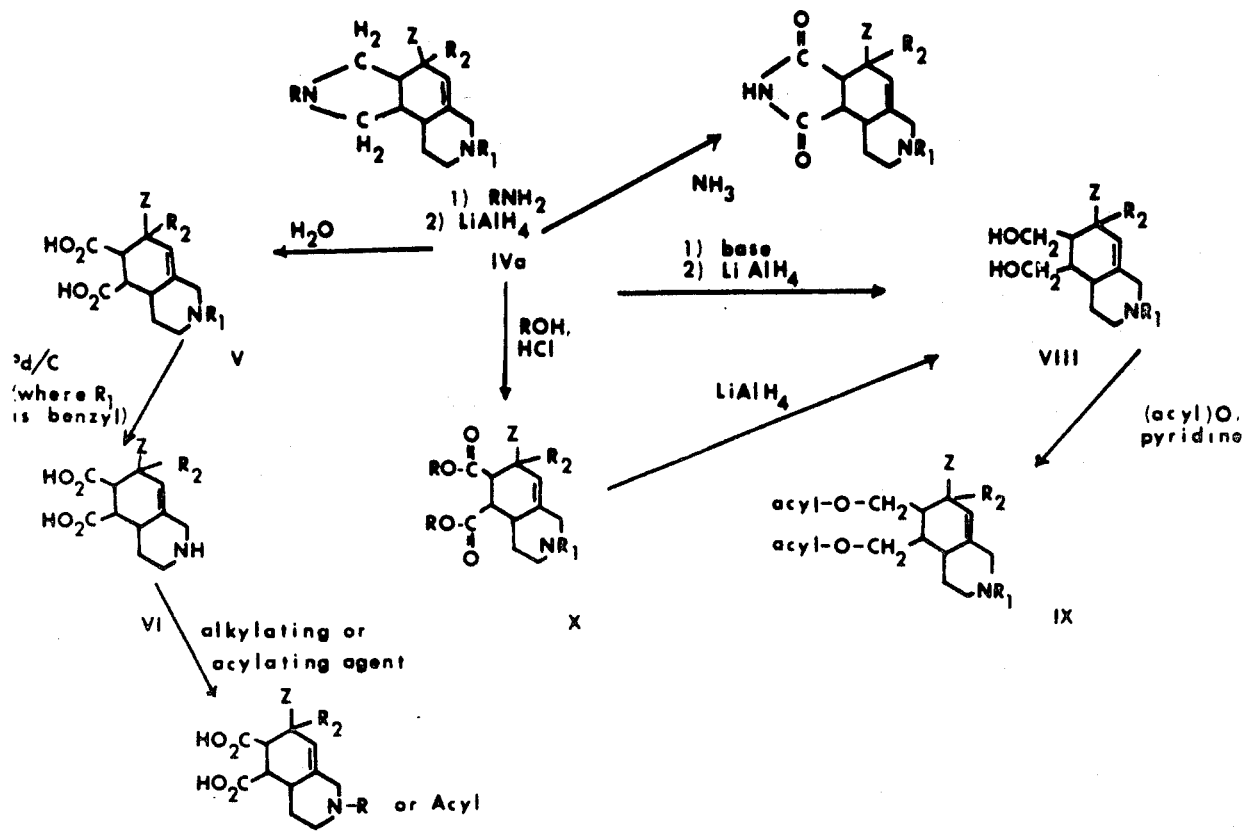

The conversion of the Diels-Alder products into the other useful compounds of this invention is also achieved by utilizing the following standard chemical procedures.

Thus where X and/or Y are carboalkoxy, carbonyl, or carboxy groupings, a LiAlH$_4$ reduction gives the corresponding alcohol (Gaylord, "Reductions with Complex Metal Hydrides" or Organic Reactions, VI, p. 469, Wiley).

Where X and/or Y are carboxamido, cyano, imino, or imido, a LiAlH$_4$ reductions cause the formation of the corresponding amine.

The above formed alcohols and amine may be converted to the corresponding esters and amides by reaction with an anhydride [(RCO)$_2$O] in pyridine. (Shriner & Fuson, "Identifications of Organic Compounds," p. 165 and 177).

The maleic anhydride Diels-Alder Adduct may be reacted with an amine, water or an alcohol (ROH) depending upon the reaction conditions to give an imide, dicarboxylic acid (water and heat), mono-esterified carboxylic acid (ROH and heat) or diester (ROH, HCl and heat) (Rodd, "Chemistry of Carbon Compounds" Vol. IB, p. 974, Elsevier).

In carrying out the initial process of this invention, a tertiary amine is employed. In order to obtain the useful secondary amines or compounds which are readily prepared from secondary amines, a tertiary benzyl amine is employed in the Diels-Alder Reaction and removed by utilizing a catalytic amount of palladium on charcoal in an organic solvent such as ethanol in the presence of hydrogen. This reaction is of special interest, since one would expect the double bond to be reduced simultaneously; however, such is not the case and high yields of debenzylated olefin is obtained.

The resultant secondary amines are converted to other useful tertiary amines by alkylation using alkylating agents such as dimethyl sulfate, methyl iodide, etc. or amides by acylation using acylating agents such as acetyl chloride, propionic anhydride, etc.

The 1,2,3,4,4a,5,6,7-octahydro-7-aryl-isoquinolines of this invention and their pharmaceutically acceptable acid addition salts have been found to be highly useful as antiflammatory agents, blood pressure lowering agents, antianginal agents and antiarrhythmic agents in mammals, such as cattle, dogs, sheep, etc. when administered in amounts ranging from about 0.3 mg to about 15 mg per kg of body weight per day. A preferred dosage regimen for optimum results would be from about 0.6 mg to about 10 mg per kg of body weight per day, and such dosage units are employed that a total of from about 20 mg to about 280 mg of active ingredient for a subject of about 70 kg body weight are administered in a 24 hour period preferrably, 40 to 140 mg. The compounds of the present invention in the described dosages are intended to be administered orally; however, other routes such as rectally, intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

1,2,3,6-Tetrahydro-1-methyl-5-styrylpyridine, hydrochloride a. To a solution of 20 g (0.1 mole) of α-(3-pyridyl)-acetophenone [JACS 82, 472 (1960)] in 150 ml of 50% aqueous ethanol at 35°–40°C is added 3.8 g (0.1 mole) sodium borohydride in portions (cooling to below 40°C). Stirring is continued until the reaction temperature falls to 35°C. Water is then added and the crude carbinol (20 g) filtered.

b. A mixture of crude 2-(3-pyridyl)-1-phenylethanol (20 g), glacial acetic acid (200 ml) and concentrated HCl (50 ml) is refluxed for 16 hours, then evaporated to dryness in vacuo. The oily hydrochloride is taken up in water, extracted with ether and methylene chloride, and then liberated with bicarbonate. Extraction (CH$_2$Cl$_2$) and drying (K$_2$CO$_3$) affords 13 g of β-(3-pyridyl)styrene.

c. Without purification β-(3-pyridyl)styrene is treated with 10 ml of methyl iodide in 100 ml of absolute ethanol at 40°C for a few minutes, then cooled. Addition of ether causes separation of 10.4 g of the crystalline methiodide (32%).

d. A solution of β-(3-pyridyl)styrene, methiodide (10.4 g, 0.032 mole) in 200 ml of 50% aqueous methanol at 40° is treated in portions with 6.0 g (0.16 mole) sodium borohydride, then stirred at 35°C for 2 hours. The mixture is cooled and extracted with ether, dried (KOH and K$_2$CO$_3$), and evaporated to yield 6.0 g (94%) of a yellow oil which crystallizes slowly at 0°C.

e. 1,2,3,6-Tetrahydro-3-styryl-1-methylpyridine, hydrochloride is prepared by treating the free base (25 g) in 400 ml of isopropanol with concentration HCl in isopropanol. Cooling at 0°C affords on drying of the filtered salt in vacuo, 28 g (95%) of the named compound.

A 10 g sample of the crude hydrochloride is recrystallized twice to afford an analytical sample (3.3 g, 31%), m.p. 237°–238°C.

Anal. Calcd. for C$_{14}$H$_{17}$N . HCl: C, 71.33; H, 7.70; N, 5.94; Cl, 15.04. Found: C, 71.47; H, 7.94; N, 5.93; Cl, 15.09.

EXAMPLES 2–5

According to the method of Example 1, if one substitutes in place of the α-(3-pyridyl)acetophenone, the following compounds:

α-(3-pyridyl)-m-isopropylacetophenone,
α-(3-pyridyl)-o-chloropropylacetophenone,
α-(3-pyridyl)-p-trifluoromethylacetophenone, and
α-(3-pyridyl)-p-carbomethoxyacetophenone, one obtains the hydrochlorides of:

1,2,3,6-tetrahydro-1-methyl-5-m-isopropylstyrylpyridine,
1,2,3,6-tetrahydro-1-methyl-5-o-chlorostyrylpyridine,
1,2,3,6-tetrahydro-1-methyl-5-p-trifluoromethylstyrylpyridine, and
1,2,3,6-tetrahydro-1-methyl-5-p-carbomethoxystyrylpyridine, respectively.

EXAMPLES 6–9

According to the method of Example 1, if one substitutes in place of the methyliodide, the following compounds
ethyl iodide,
phenethyl iodide,
isopropyl iodide and
benzyl iodide,
one obtains the hydrochlorides of:
1,2,3,6-tetrahydro-1-ethyl-5-styrylpyridine,
1,2,3,6-tetrahydro-1-phenethyl-5-styrylpyridine,
1,2,3,6-tetrahydro-1-isopropyl-5-styrylpyridine, and
1,2,3,6-tetrahydro-1-benzyl-5-styrylpyridine, respectively.

EXAMPLE 10

1,2,3,6-Tetrahydro-5-(p-methoxystyryl)-1-methylpyridine, hydrochloride a. To a solution of 3 moles of lithium diisopropylamide in 3 liters ether is added 3 moles of β-picoline. After ½ hour, a solution of 1 mole methyl anisate in ether is added dropwise. After 1 hour under reflux, the mixture is cooled and decomposed with water. After all the lithium has dissolved, the layers are separated. The organics are washed with water, dried (magnesium sulfate) and distilled. The product is collected at 155°–165°C at 0.3 mm Hg and recrystallized from benzene-pet ether to yield 88 g (39%) 4-methoxy-α-(3-pyridyl)-acetophenone. [Miller, Osuch, Goldberg, and Levine, JACS, 78, 674 (1956) and Raynolds and Levine, JACS, 82, 472 (1960)].

b. To a solution of 25 g (0.11 moles) of the above acetophenone in 250 ml 50% aqueous ethanol stirring in an ice bath is added 4.2 g (0.11 moles) sodium borohydride in portions (T ≤ 30°C). This is stirred for 1 hour at room temperature. Water is added and filtration affords 22 g (88%) 1-(4-methoxyphenyl)-2-(3-pyridyl)-ethanol.

c. A solution of 58 g (0.253 moles) of the above alcohol in 600 ml glacial acetic acid and 150 ml hydrochloric acid is stirred under reflux overnight. The solution is cooled and evaporated in vacuo. Benzene is added and evaporated twice. The yellow solid residue is dissolved in water and extracted with ether, dichloromethane, and again ether to remove impurities. The aqueous layer is basified with sodium bicarbonate and extracted with dichloromethane. The organic layers are dried (sodium carbonate) and evaporated to give a quantitative yield of 3-(p-methoxystyryl)pyridine.

d. The above styrene (53 g, 0.253 moles) is dissolved in 350 ml acetonitrile with heating. Methyl iodide (0.9 moles) is added dropwise over 15 minutes with stirring. This is refluxed for 1 hour and cooled to room temperature. Ether is added and the solution is allowed to stand in a cold room overnight. Filtration yields 55.6 g (63%) crystalline 3-(p-methoxystyryl)-pyridine, methiodide.

e. To 55.6 g (0.157 moles) of the above methiodide stirring in 1 liter 50% aqueous methanol is added 18 g (0.47 moles) sodium borohydride in portions over 1 hour (T ≤ 35°C). This is stirred for 1 hour. Water is added and white solid filtered. This solid is dissolved in ether and dried (magnesium sulfate). Evaporation in vacuo yields 27.5 g 1,2,3,6-tetrahydro-5-(p-methoxystyryl)-1-methylpyridine. The aqueous layer is extracted with ether. The organic layer is dried (magnesium sulfate and evaporated to yield an additional 5 g product.

f. A 5 g sample of the above tetrahydropyridine is dissolved in ether. With stirring, hydrochloric acid in isopropanol-ether is added until the solution is acidic to pH paper. The white solid is filtered to yield 5.5 g (85%) 1,2,3,6-tetrahydro-5-(p-methoxystyryl)-1-methylpyridine, hydrochloride.

Recrystallization of 5.5 g from isopropanol-ether affords an analytical sample, 1.7 g, mp 177°–187°C (d).

Anal. Calcd for $C_{15}H_{19}NO \cdot HCl$: C, 67.79; H, 7.59; N, 5.27; Cl, 13.34 Found: C, 67.92; H, 7.38; N, 5.05; Cl, 13.11.

EXAMPLE 11

3a,4,6,7,8,9,9a,9b-Octahydro-4-(p-methoxyphenyl)-2,7-dimethyl-2H-pyrrolo[3,4-f]isoquinoline-1,3-dione A solution of 15 g (0.065 moles) 1,2,3,6-tetrahydro-1-methyl-5-p-methoxystyrylpyridine (free base), 15 g N-methylmaleimide, 150 ml toluene and 20 mgs hydroquinone is refluxed under nitrogen overnight. The solution is allowed to cool and evaporate. Benzene is added and evaporated twice. Water is added, and the oil is extracted with benzene. The organic layers are evaporated. The residue crystallizes and filtration and washing with ether yields 7.85 g 3a,4,6,7,8,9,9a,9b-octahydro-4-(p-methoxyphenyl)-2,7-dimethyl-2H-pyrrolo[3,4-f]-isoquinoline-1,3-dione. Chromatography of the mother liquor on basic alumina (activity II) yields an additional 3.2 g (50%) cyrstals.

Recrystallization of 1.8 g from dichloromethane-hexane affords the analytical sample, 1.3 g, mp 129°–130°C.

Anal. Calcd for $C_{20}H_{24}N_2O_3$: C, 70.56; H, 7.11; N, 8.23. Found: C, 70.67; H, 7.00; N, 7.94.

EXAMPLE 12

1,2,3,4,4a,5,6,7-Octahydro-2-methyl-7-phenyl-5,6-isoquinolinedicarboxylic acid, hydrochloride 1,2,3,6-Tetrahydro-1-methyl-5-styrylpyridine (23 g, 0.098 mole) and maleic anhydride (60 g, 0.61 mole) in 400 ml of a 1:1 mixture of acetic anhydride and acetic acid is treated with a few crystals of hydroquinone, brought to reflux for a few minutes, then cooled to room temperature over 1.5 hours. Benzene (1.5 l.) is added to the dark mixture and the gummy black precipitate is triturated until granular. After filtration and thorough washing with benzene, the solid is suspended in water overnight, then heated for 4 hours on steam. A decolorizing carbon is added, the hot mixture is filtered and the dark solution is evaporated to a viscous oil in vacuo. Crystallization from approximately 200 ml isopropanol affords 11 g of adduct (32%), a single isomer as judged from its NMR spectrum. Two recrystallizations afford an analytical sample, mp 218°–223°C. (dec.).

Anal. Calcd. for $C_{18}H_{21}O_4N \cdot HCl$: C, 61,45; H, 6.30; N, 3.98; Cl, 10.08. Found: C, 61.27; H, 6.15; N, 3.95; Cl, 10.14.

EXAMPLES 13–17

According to the method of Example 12, if one substitutes in place of the maleic anhydride, the following compounds:
acrylic acid,
acrylonitrile,
ethyl acrylate,
nitroethylene and
p-quinone,
one obtains the hydrochlorides of:
1,2,3,4,4a,5,6,7-octahydro-2-methyl-7-phenyl-6-carboxyisoquinoline,
1,2,3,4,4a,5,6,7-octahydro-2-methyl-7-phenyl-6-cyano-isoquinoline,
1,2,3,4,4a,5,6,7-octahydro-2-methyl-7-phenyl-6-carboethoxyisoquinoline,
1,2,3,4,4a,5,6,7-octahydro-2-methyl-7-phenyl-6-nitro-isoquinoline, and
1,2,3,4,6,6a,7,10,10a,10b-decahydro-3-methyl-6-phenylbenz[f]isoquinoline-7,10-dione, respectively.

EXAMPLE 18

Dimethyl 1,2,3,4,4a,5,6,7-Octahydro-2-methyl-7-phenyl-5,6-isoquinolinedicarboxylate A solution of 18.5 g Diels-Alder adduct of Example 12 in 1 liter methanol with 20 ml hydrochloric acid in isopropanol is refluxed overnight. The solution is cooled and evaporated. The residue is dissolved in water. This is basified with 10% sodium hydroxide solution and extracted with dichloromethane. The organic layers are dried (potassium carbonate) and evaporated to yield 12 g (63%) oily diester.

EXAMPLE 19

According to the method of Example 18, if one substitutes in place of the methanol, the following compounds:
ethanol and 2-methylpropanol
one obtains the corresponding diethyl and di-2-methylpropyl carboxylate.

EXAMPLE 20

1,2,3,4,4a,5,6,7-Octahydro-2-methyl-7-phenyl-5,6-isoquinoline dimethanol

A solution of 12 g (0.035 moles) of the diester of Example 18 in 70 ml dichloromethane:ether (1:1) is added to a slurry of 2.66 g (0.07 moles) lithium aluminum hydride in 300 ml dichloromethane:ether (1:1) with stirring under nitrogen. This is refluxed for 4 hours and cooled to room temperature. Saturated sodium carbonate solution is added until the mixture turned white. This is filtered and the solids are washed with dichloromethane and 10% ethanol in dichloromethane. The filtrates are evaporated to yield 8.3 g of 1,2,3,4,4a,5,6,7-octahydro-2-methyl-7-phenyl-5,6-isoquinolinedimethanol. Crystallization from ethyl acetate yields 3.6 g (35%) pure diol.

Recrystallization of 1.5 g from methanol-ethyl acetate affords the analytical sample, 1 g, mp 175°–177°C.

Anal. Calcd for $C_{18}H_{25}NO_2$: C, 75.22; H, 8.77; N, 4.87. Found: C, 75.09; H, 9.00; N, 4.59.

EXAMPLES 21–23

According to the method of Example 20, if one substitutes in place of the dimethyl 1,2,3,4,4a,5,6,7-octahydro-2-methyl-7-phenyl-5,6-isoquinoline dicarboxylate, the following compounds:

dimethyl-1,2,3,4,4a,5,6,7-octahydro-2-ethyl-7-m-chloro-phenyl)-5,6-isoquinolinedicarboxylate, dimethyl 1,2,3,4,4a,5,6,7-octahydro-2-methyl-7-o-methylphenyl-6-cyano-isoquinolinedicarboxylate, and dimethyl 1,2,3,4,4a,5,6,7-octahydro-2-benzyl-7-m-trifluoromethylphenyl-5,6-dicyano-isoquinolinedicarboxylate, one obtains:

1,2,3,4,4a,5,6,7-octahydro-2-ethyl-7-m-chlorophenyl-5,6-isoquinolinedimethanol, 1,2,3,4,4a,5,6,7-octahydro-2-methyl-7-o-methylphenyl-6-aminomethyl-isoquinolinedimethanol, and 1,2,3,4,4a,5,6,7-octahydro-2-benzyl-7-m-trifluoromethylphenyl-6,7-diaminomethyl-isoquinolinedimethanol, respectively.

EXAMPLE 24

1,2,3,4,4a,5,6,7-Octahydro-2-methyl-7-phenyl-5,6-isoquinolinedimethanol, diacetate ester, hydrochloride To a solution of 36 g (0.013 moles) of the compound prepared in Example 20 in 40 ml pyridine at 0°C is added 20 ml acetic anhydride dropwise with stirring. This is stirred for 1 hour at 0°C and overnight at room temperature. The solution is evaporated. The residue is dissolved in ether and stirred with saturated sodium bicarbonate solution for ½ hour. The layers are separated and the aqueous is extracted with ehter. The organic layers are dried (magnesium sulfate) and evaporated to yield 4 g (83%), 1,2,3,4,4a,5,6,7-octahydro-2-methyl-7-phenyl-5,6-isoquinolinedimethanol, diacetate ester.

The diacetate ester is dissolved in ether and hydrochloric acid in isopropyl alcohol-ether is added until the solution is acidic to pH paper. The solution is filtered and the solid is recrystallized from isopropyl alcohol-ether to yield 3.2 (72%) of the hydrochloride salt.

Recrystallization of 2 g from isopropyl alochol-ether affords an analytical sample, 1.5 g, mp 181°–182°C.

Anal. Calcd for $C_{23}H_{30}NO_4Cl$: C, 64.78; H, 7.41; N, 3.43; Cl, 8.69. Found: C, 64.82; H, 7.16; N, 3.38; Cl, 8.75.

EXAMPLE 25

1,2,3,4,4a,5,6,7-Octahydro-7-(p-methoxyphenyl)-2-methyl-5,6-isoquinolinedimethanol, diacetate ester, hydrochloride a. A solution of 16 g (0.06 moles) 1,2,3,6-tetrahydro-1-methyl-5-p-methoxystyrylpyridine, 37 g ground maleic anhydride, 130 ml glacial acetic acid, 130 ml acetic anhydride, and 50 mg hydroquinone is refluxed under nitrogen for ½ hour. The solution is allowed to cool and evaporate to an oil. Benzene is added and evaporated twice. The crude Diels-Alder adduct is dissolved in 500 ml methanol and 20 ml hydrochloric acid in isopropanol and refluxed for 18 hours. The solution is allowed to cool and evaporate. The residue is dissolved in water and extracted with ether and dichloromethane. The aqueous is basified with 10% sodium hydroxide and extracted with dichloromethane. These organic layers are dried (sodium carbonate) and evaporated to yield 10 g of the diester. The organic layers from the first extraction are evaporated and the residue is dissolved in water and extracted with ether. The aqueous portion is basified and extracted as above to yield an additional 9.4 g (86%) of the diester.

b. A solution of 15 g (0.04 moles) of the diester in 100 ml dichloromethane:ether (1:1) is added to a slurry of 3.14 g lithium aluminum hydride in 300 ml dichloromethane:ether (1:1) stirring under nitrogen. This is refluxed for 4 hours and allowed to cool to room temperature. Saturated sodium carbonate solution is added until the solution turned white. This is filtered and the solids are washed with dichloromethane and 10% ethanol in dichloromethane. The filtrates are evaporated to yield, respectively, 7g and 4 g (85%) crude 1,2,3,4,4a,5,6,7-octahydro-7-(p-methoxyphenyl)-2-methyl-5,6-isoquinolinedimethanol.

c. To a solution of 4.3 g (0.0135 moles) of pure isoquinolinedimethanol one obtains from chromatography of the 7 g sample on basic alumina (activity III) in 40 ml pyridine at 0°C is added 20 ml acetic anhydride dropwise. This is stirred for 1 hour at 0°C and overnight at room temperature. The solution is evaporated and benzene is added and evaporated twice. The residue is dissolved in ether and stirred with saturated sodium bicarbonate solution for ½ hour. The layers are separated and the aqueous portion extracted with ether. The organic layers are dried (magnesium sulfate) and evaporated to yield 4 g (74%) 1,2,3,4,4a,5,6,7-octahydro-7-(p-methoxyphenyl)-2-methyl-5,6-isoquinolinedimethanol, diacetate ester. A 4 g sample is dissolved in ether and hydrochloric acid in isopropanol-ether is added until the solution is acidic to pH paper. The solid is filtered and recrystallization from isopropanol-ether yields 4.4 g (100%) the hydrochloride.

Recrystallization from isopropanol-ether affords an analytical sample, 2.4 g, mp 164°–165°C.

Anal. Calcd for $C_{23}H_{32}NO_5Cl$: C, 63.07; H, 7.36 N, 3.20; Cl, 8.09. Found: C, 62.67; H, 7.06; N, 3.05; Cl, 8.20.

EXAMPLE 26

1,3,3a,4,6,7,8,9,9a,9b-Decahydro-4-(p-methoxyphenyl)-2,7-dimethyl-2H-pyrrolo[3,4-f]isoquinoline A solution of 6.7 g (0.02 moles) of 3a,4,6,7,8,9,9a,9b-octahydro-4-(p-methoxyphenyl)-2,7-dimethyl-2H-pyrrolo[3,4-f]-isoquinoline-1,3-dione in 100 ml of dichloromethane-ether (1:1) is added to a slurry of 3 g (0.08 moles) lithium aluminum hydride in 300 ml dichloromethane-ether (1:1) under nitrogen. This is refluxed for 18 hours. Saturated sodium carbonate solution is added at room temperature until the reaction is white. The salts are filtered and washed with dichloromethane. The combined filtrates are evaporated to yield 5.5 g (90%) 1,3,3a,4,6,7,8,9,9a,9b-decahydro-4-(p-methoxyphenyl)-2,7-dimethyl-2H-pyrrolo[3,4-f]isoquinoline. This is dissolved in isorpopanol-ether, and hydrochloric acid in isopropanol is added until the solution is acidic to pH paper. Excess ether is added and the white solid product is filtered.

EXAMPLE 27

1,2,3,4,4a,5,6,7-Octahydro-7-(p-methoxyphenyl)-5,6-isoquinolinedimethanol, diacetate ester, oxalate An 11 g (0.023 mole) sample of 2-benzyl-1,2,3,4,4a,5,6,7-octahydro-7-(p-methoxyphenyl)-5,6-isoquinolinedimethanol, diacetate ester, is debenzylated in 200 ml absolute ethanol with 1 g palladium on carbon. After 4 days at 30 psi on the Parr apparatus, the sample is filtered and the catalyst is washed with ethanol. The combined filtrates are evaporated. Column chromatography (basic alumina, activity II in chloroform) yields about 4.6 g (52%) debenzylated diacetate, and 4.6 g of the starting benzyl compound. A 2.3 g (0.006 mole) sample of this debenzylated material is dissolved in 10 ml isopropanol and 0.67 g (0.005 moles) oxalic acid is next added. This is swirled and heated slightly to dissolve the acid. The addition of ether affords about 2.5 g (100%) crystalline 1,2,3,4,4a,5,6,7-octahydro-7-(p-methoxyphenyl)-5,6-isoquinolinedimethanol, diacetate ester, oxalate salt (1:1). Further recrystallization of 2.5 g from methanolisopropanol-ether gives and analytically pure sample, 0.95 g, mp 105°–110° C.

EXAMPLES 28–29

According to the method of Example 27, if one substitutes in place of the 2-benzyl-1,2,3,4,4a,5,6,7-octahydro-7-(p-methoxyphenyl)-5,6-isoquinolinedimethanol, diacetate ester, the following compounds:

1,2,3,4,4a,5,6,7-octahydro-7-phenyl-5,6-isoquinolinedimethanol, dipropionate ester, and dimethyl-1,2,3,4,4a,5,6,7-octahydro-7-phenyl-5,6-isoquinolinedicarboxylate, one obtains the corresponding debenzylated compound.

EXAMPLE 30

Preparation of capsule formulation

| Ingredient | Milligrams per Capsule |
|---|---|
| 1,2,3,4,4a,5,6,7-octahydro-7-(p-methoxyphenyl)-5,6-isoquinolinedicarboxylic acid | 200 |
| Starch | 95 |
| Magnesium stearate | 5 |

The active ingredient, starch and magnesium stearate are blended together. The mixture is used to fill hard shell capsules of a suitable size at a fill weight of 300 milligrams per capsule.

EXAMPLE 31

Preparation of tablet formulation

| Ingredient | Milligrams per Tablet |
|---|---|
| 1,2,3,4,4a,5,6,7-octahydro-2-methyl-7-phenyl-5,6-isoquinoline dimethanol | 100 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 32

Preparation of oral syrup formulation

| Ingredient | Amount |
|---|---|
| 1,2,3,4,4a,5,6,7-octahydro-7-(p-methyoxyphenyl)-2-methyl-5,6-isoquinoline dicarboxylic | 500 mg |
| Sorbitol solution (70% N.F.) | 40 ml |
| Sodium benzoate | 150 mg |
| Sucaryl | 90 mg |
| Saccharin | 10 mg |
| Red Dye (F.D. & C. No. 2) | 10 mg |
| Cherry flavor | 50 mg |
| Distilled water qs to | 100 ml |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphate, citrates or tartrates may be added as buffers. Preservatives may include the parabens, sorbic acid and the like and other flavors and dyes may be used in place of those listed above.

What is claimed is:
1. A compound of the formula:

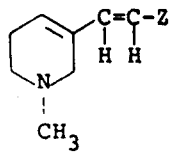

wherein Z is phenyl or methoxyphenyl; and pharmaceutically acceptable salts thereof.

2. The compound of claim 1 having the name 1,2,3,6-tetrahydro-1-methyl-5-styrylpyridine, hydrochloride.

3. The compound of claim 1 having the name 1,2,3,6-tetrahydro-5-(p-methoxystyryl)-1-methylpyridine, hydrochloride.

4. The compound having the name 1,2,3,6-tetrahydro-1-methyl-5-m-isopropylstyrylpyridine, hydrochloride.

5. The compound having the name 1,2,3,6-tetrahydro-1-methyl-5-o-chlorostyrylpyridine, hydrochloride.

6. The compound having the name 1,2,3,6-tetrahydro-1-methyl-5-p-trifluoromethylstyrylpyridine, hydrochloride.

7. The compound having the name 1,2,3,6-tetrahydro-1-methyl-5-p-carbomethoxystyrylpyridine, hydrochloride.

8. The compound having the name 1,2,3,6-tetrahydro-1-ethyl-5-styrylpyridine, hydrochloride.

9. The compound having the name 1,2,3,6-tetrahydro-1-isopropyl-5-styrylpyridine, hydrochloride.

* * * * *

UNITED STATES PATENT AND TRADEMARK OFFICE
CERTIFICATE OF CORRECTION

PATENT NO. : 3,953,434
DATED : April 27, 1976
INVENTOR(S) : Hauck et al.

It is certified that error appears in the above-identified patent and that said Letters Patent are hereby corrected as shown below:

In the inventors' names, "Frederick" should read --Frederic--.

Col. 11, line 58, "ehter" should read --ether--.

Col. 14, line 63, "Phosphate" should read --Phosphates--.

Signed and Sealed this

Twenty-eighth Day of September 1976

[SEAL]

Attest:

RUTH C. MASON
Attesting Officer

C. MARSHALL DANN
Commissioner of Patents and Trademarks